(12) United States Patent
Blomqvist et al.

(10) Patent No.: US 8,690,787 B2
(45) Date of Patent: Apr. 8, 2014

(54) IMPLANTABLE CORONARY PERFUSION MONITORING DEVICE

(75) Inventors: Andreas Blomqvist, Spånga (SE); Karin Järverud, Solna (SE); Michael Broomè, Ekerö (SE)

(73) Assignee: St. Jude Medical AB, Jarfalla (SE)

( * ) Notice: Subject to any disclaimer, the term of this patent is extended or adjusted under 35 U.S.C. 154(b) by 326 days.

(21) Appl. No.: 13/265,722

(22) PCT Filed: Apr. 29, 2009

(86) PCT No.: PCT/SE2009/000223
§ 371 (c)(1),
(2), (4) Date: Oct. 21, 2000

(87) PCT Pub. No.: WO2010/126404
PCT Pub. Date: Nov. 4, 2010

(65) Prior Publication Data
US 2012/0083703 A1    Apr. 5, 2012

(51) Int. Cl.
*A61B 5/02*   (2006.01)
(52) U.S. Cl.
USPC ............................ 600/486; 600/500; 600/485
(58) Field of Classification Search
USPC .................................................. 600/486, 500
See application file for complete search history.

(56) References Cited

U.S. PATENT DOCUMENTS

| | | | |
|---|---|---|---|
| 4,821,735 A | 4/1989 | Goor et al. | |
| 4,834,107 A | 5/1989 | Warner | |
| 5,054,493 A | 10/1991 | Cohn et al. | |
| 5,211,177 A | 5/1993 | Chesney et al. | |
| 5,766,127 A * | 6/1998 | Pologe et al. | 600/310 |
| 6,122,535 A * | 9/2000 | Kaestle et al. | 600/322 |
| 6,315,735 B1 | 11/2001 | Joecken et al. | |
| 7,951,129 B2 | 5/2011 | Chinchoy | |
| 2009/0275854 A1 | 11/2009 | Zielinski et al. | |

FOREIGN PATENT DOCUMENTS

EP   1 518 560 A1   3/2005

OTHER PUBLICATIONS

U.S. Appl. No. 12/809,255, filed Jun. 18, 2010.

* cited by examiner

*Primary Examiner* — Navin Natnithithadha
*Assistant Examiner* — Etsub Berhanu (57) ABSTRACT

An implantable coronary perfusion monitoring device for in-vivo determination of a coronary perfusion index (CPI) indicative of the coronary perfusion of a heart has a time measurement unit to determine a blood pressure reflection wave measure t indicating the timely position in the heart cycle of the maximum of a reflected blood pressure wave and in a time period starting at a preset point of time in systole and ending at a local maximum of blood pressure following aortic valve closure and, a diastolic peak pressure measurement unit adapted to determine a diastolic peak blood pressure measure DPP related to diastolic aortic peak pressure and a systolic arterial pressure measurement unit adapted to determine a systolic arterial blood pressure measure SAP related to systolic arterial pressure, and a coronary perfusion index calculating unit adapted to determine said coronary perfusion index CPI as (t·DPP)/SAP.

24 Claims, 6 Drawing Sheets

IMPLANTABLE CORONARY PERFUSION MONITORING DEVICE

BACKGROUND OF THE INVENTION

1. Field of the Invention

The present invention relates to an implantable coronary perfusion monitoring device according to the preamble of the independent claim.

2. Description of the Prior Art

For ischemic patients, the normal compensatory mechanism in autoregulating blood flow is generally decreased by the underlying cardiovascular disease (arteriosclerosis). It is therefore even more important for ischemic patients to get optimized coronary perfusion. This perfusion is adversely affected by arteriosclerosis due to:

A) the time-shift of the peripherally reflected pressure ways, and

B) the decreased compliance of the aorta, as described below.

In short, the present invention is inter alia based upon the theory of the so-called "Windkessel effect" and peripherally reflected pressure waves, resulting in a measure calculated through the use of various sensors (e.g. impedance sensors) which very effectively can monitor the conditions which are crucial for a good coronary perfusion.

Vascular mechanical properties are carefully matched with cardiac position, heart rate and timing of contraction in a young healthy person (or animal) to minimize afterload and maximize coronary perfusion. The pressure curve in the first part of aorta is determined not only by cardiac and local vascular properties, but also by the properties of the more distal elastic arteries, which is referred to as the "Windkessel effect" and reflection of pressure waves in the periphery (mainly in bifurcations and high resistance vessels).

The elastic (large) arteries expand during systolic ejection of blood from the left ventricle and recoil in diastole. The physiologic meaning of this is to decrease the rise of pressure during ejection and thereby facilitate ejection (i.e. minimize afterload) and also to increase pressure during diastole improving coronary perfusion pressure at the time when the heart is relaxed and can be perfused. The time constant of recoil is in a healthy person perfectly matched.

With increasing age and stiffening of the arteries both the time constant and the volume of blood that can be "stored" during systole decrease.

The reflection of pressure waves has a similar physiologic effect. The pressure waves (5-10 m/s) travel much faster than blood flow (<1 m/s). This means that waves reflected in the periphery come back to the heart during each ongoing beat. The wave speed is affected by many factors including blood pressure and stiffness of the vessels. The reflection coefficient is determined by the matching of vascular impedances. In a healthy person bifurcations are almost perfectly matched to avoid reflection of forward travelling waves. The main source of reflection in healthy person therefore is peripheral resistance vessels (arteriole). The summed effect of the reflected pressure waves is to increase diastolic pressure and facilitate coronary perfusion as above, while maintaining a low afterload.

With increasing age and arteriosclerosis reflection coefficients in vascular bifurcations increase and since wave speed also increases this causes the reflected waves to arrive back in the aortic root earlier (during early systolic ejection), thereby increasing afterload (lowering stroke volume) and causing premature closure of the aortic valve, without contributing to coronary perfusion. This is illustrated by the curves in FIG. 1.

Figure 1:
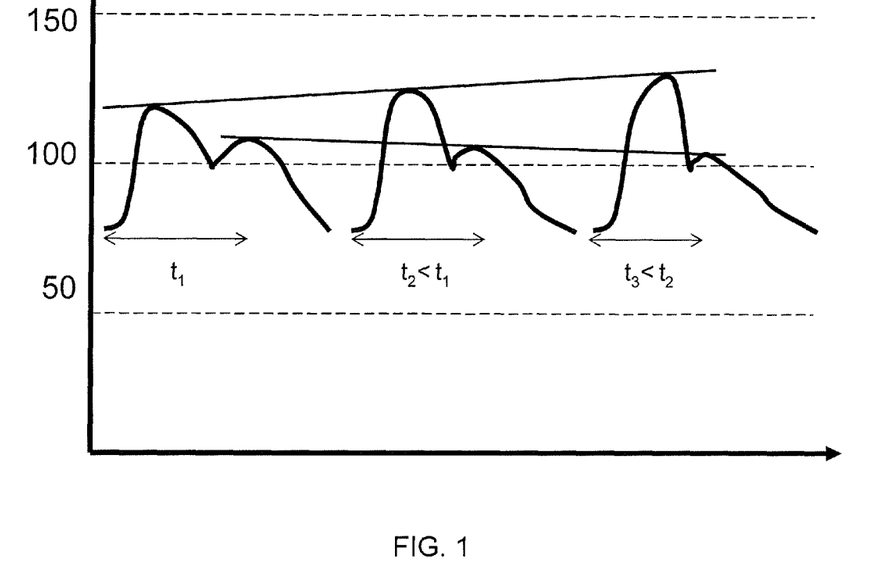
FIG. 1 shows curves illustrating pressure curves for patients of different ages.

In the Figure the evolution of the aortic pressure curve with age is seen. The aortic pressure is denoted at the y-axis, and time is denoted at the x-axis. The left curve represents the pressure curve of a younger individual, the middle curve represents a middle-aged individual and the right curve an older individual. As clearly visible from the curves the point of time ($t_1$, $t_2$, $t_3$) for the maximum pressure during diastole is earlier the older patient is. Furthermore, the difference between the maximum pressure values is increasing with age, which is illustrated by the lines in the Figure.

The intricate pathophysiology discussed above is extremely important when understanding the effects of cardiovascular disease. Arteriosclerosis is a problem far more complicated than "vascular stenosis". The above mentioned phenomena are not only related to arteriosclerosis, but also to hypertension per se since vascular stiffness is non-linear. Wave speed and stiffness increase with increasing pressure. This may be functional in exercise with increasing heart rate and a modest rise in blood pressure, since the matching then is maintained, but is usually an unwanted effect in hypertensive disease.

When contemplating the facts above it becomes clear that optimal cardiovascular matching is dependant on heart rate, timing of ejection, blood pressure and vascular properties. These factors are all changing in short-term (ischemia, stress) and long-term (arteriosclerosis, remodelling, disease progression) in cardiac patients. It makes sense to monitor this matching both aiming to optimize treatment and also possibly warn the patient or doctor.

In the following some patent documents are listed which are related to some of the aspects discussed above.

U.S. Pat. No. 4,821,735 relates to a method and apparatus for detecting myocardial ischemia that monitors the systemic vascular resistance and detects the presence of myocardial ischemia when the systemic vascular resistance increases by at least sixty percent over a base line value.

The detection involves monitoring the arterial pressure to get a blood pressure signal. The first time derivative of the blood pressure signal is calculated and the peak of the dP/dt signal is determined. The pressure value corresponding in time to this identified peak in dP/dt is identified. The systemic vascular resistance is determined as the quotient between the identified pressure value and the peak dP/dt value.

U.S. Pat. No. 6,315,735 discloses an in-vivo technique for determination of the compliance of the vascular system downstream of a ventricle or the systemic blood flow from the blood pressure. The calculations are based upon the so-called Windkessel model.

U.S. Pat. No. 5,211,177 discloses determination of vascular impedance based upon arterial blood pressure and the modified Windkessel model.

WO-2005/014084 discloses an IMD capable of identifying periods of coronary perfusion based upon different signals collected by the IMD, such as pressure signals, oximetry signals, etc. and then to deliver a therapeutic and/or diagnostic agent to a heart during diastolic coronary perfusion for more optimal use of the agent.

There is a need for improved indication and monitoring of the status of coronary perfusion both for diagnostic and therapeutic purposes.

SUMMARY OF THE INVENTION

An object of the present invention is to achieve an improved device meeting the above demands.

In summary, the invention is based on the theory of the Windkessel effect and peripherally reflected pressure waves, and a measure is determined which very effectively monitors the conditions which are crucial for a good coronary perfusion.

The coronary perfusion index (CPI), according to the present invention, is defined as:

$$CPI = \frac{t \cdot DDP}{SAP}$$

where, t is a blood pressure reflection wave measure indicating the timely position in the heart cycle of the maximum of a reflected blood pressure wave;

DPP is a diastolic peak blood pressure measure related to diastolic aortic peak pressure, and SAP is a systolic arterial blood pressure measure related to systolic arterial pressure.

The coronary perfusion index CPI is constructed to monitor both the supply and demand side of coronary circulation and should be as high as possible. The systolic arterial pressure SAP is a measure of demand, while the diastolic peak pressure DPP is a measure of blood supply. The time t is a measure of the "biological age" of the cardiovascular system.

All three components of CPI are affected by drug therapy, pacing and other short term hemodynamic changes. It is therefore relevant to monitor both short term and long term changes in CPI with a cardiac monitoring device.

When the "biological age" of the system increases, due to arteriosclerosis or suboptimal treatment, it tends to decrease both t and DDP while SAP is increasing. The CPI index is therefore very sensitive to these changes.

In severe arteriosclerosis the maximum of the reflected (and recoil) pressure wave might occur during systole, i.e. before closure of the aortic valve. This is important to have in mind when determining a starting point for the time period t, which in some cases might be negative if the starting point is chosen too close in time to the expected point of time of the reflected pressure wave.

The above measures used to calculate CPI may be determined in a number of different ways.

According to one embodiment one or many of the measures are determined by use of impedance measurements.

According to another embodiment one or many of the measures are determined by use of blood pressure measurements.

According still another embodiment one or many of the measures are determined by a combination of different measurement techniques, e.g. by measuring blood pressure, impedance, blood flow, heart sound or electrical heart potentials.

The CPI may be used for diagnosis or for therapy management. The therapy (pacing, drug management/titration, etc.) could then be adjusted to maximize CPI.

The invention thus provides a measure that will be indicative of how well the systems for ensuring optimal coronary perfusion are functioning, depending directly upon vascular status.

Based on this knowledge, one can:

a. trend the arterial compliance over time, and thereby provide information regarding the underlying cardiovascular disease, b. optimize therapy as to maximize CPI. The therapy being one or many of pacing, drug titration, etc.

c. perform diagnostic monitoring, and d. alert patient/physician of acute worsening.

DESCRIPTION OF THE PREFERRED EMBODIMENTS

Figure 2:
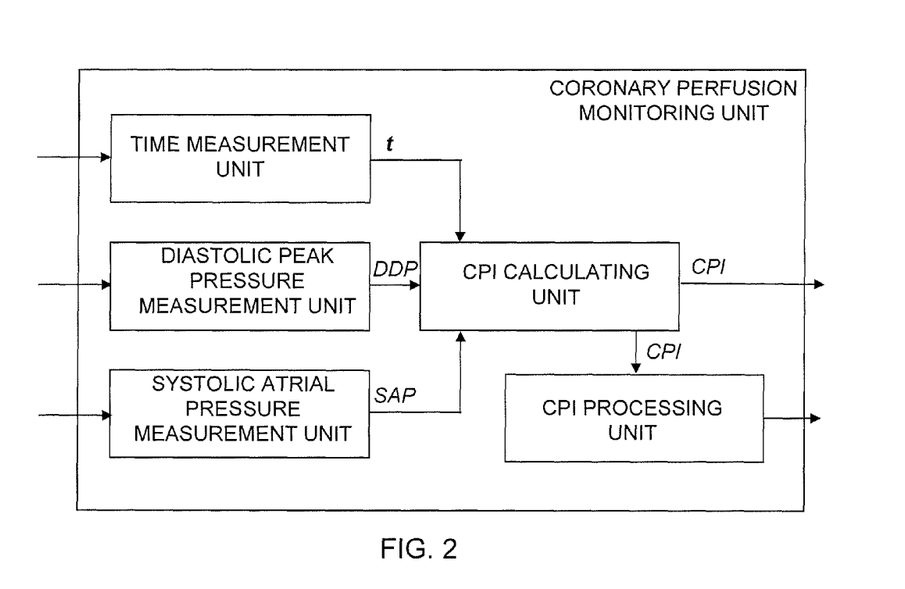
FIG. 2 is a block diagram illustrating the implantable coronary perfusion monitoring device according to the present invention.

Initially, by referring to FIG. 2, showing a block diagram of the implantable coronary perfusion monitoring device according to the present invention, the overall concept of the present invention will be discussed.

Thus, the present invention relates to an implantable coronary perfusion monitoring device for in-vivo determination of a coronary perfusion index (CPI) indicative of the coronary perfusion of a heart.

The device includes a systolic arterial pressure measurement unit adapted to determine a systolic arterial blood pressure measure SAP related to systolic arterial pressure;

a diastolic peak pressure measurement unit adapted to determine a diastolic peak blood pressure measure DPP related to diastolic aortic peak pressure, and a time measurement unit to determine a blood pressure reflection wave measure t indicating the timely position in the heart cycle of the maximum of a reflected blood pressure wave and being a time period starting at a preset point of time in systole and ending at a local maximum of blood pressure following aortic valve closure.

A coronary perfusion index calculating unit is provided adapted to determine said coronary perfusion index CPI as (t·DPP)/SAP.

The coronary perfusion index CPI is calculated by using three parameters t, DPP and SAP.

In the following each of these parameters will be separately discussed, both with regard to definitions and to measurement techniques for detecting and determining the parameters.

Although each parameter is separately discussed it is naturally assumed that all possible combinations of used measurement techniques must be contemplated when the device is structurally realized. E.g., when the time measure t is determined an impedance measurement unit is used according to one embodiment. Also when determining DPP and SAP impedance measurements may be used and it is then preferably considered that the same impedance measurement unit is used, if technically and physically feasible. The same discussion is also valid when using a blood pressure measurement unit for determining the parameters.

Time Measure t

According to one embodiment the blood pressure reflection wave measure t is a time period starting at a preset point of time in systole and ending at a local maximum of blood pressure following aortic valve closure.

As will be apparent from the following discussion it is the point of time in the heart cycle of the local maximum of the reflected blood pressure wave that is of importance, and a number of different ways to detect that point of time and to relate it to relevant and detectable events in the heart cycle will be disclosed.

Figure 3:
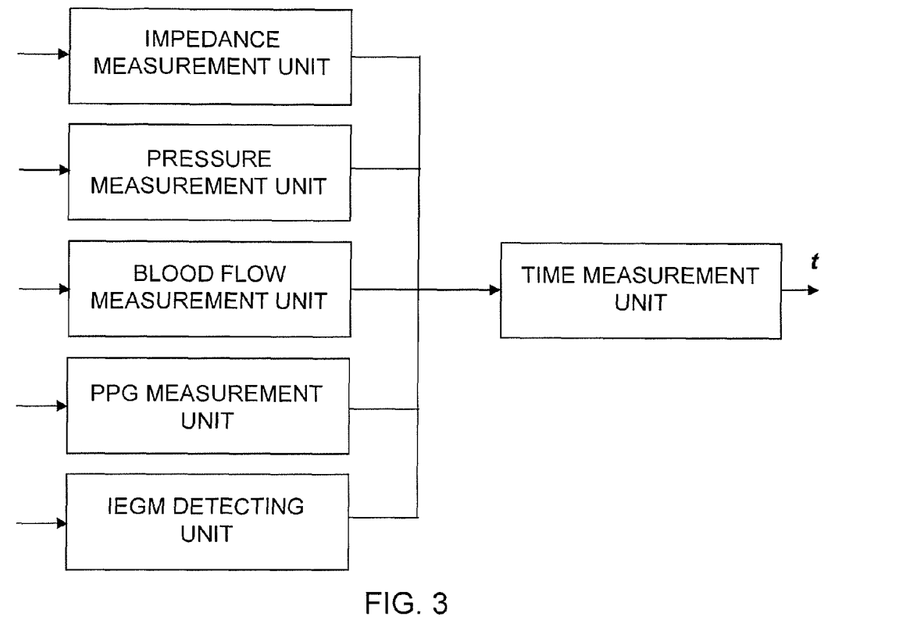
FIG. 3 is a block diagram illustrating different embodiments for determining a time measure in accordance with the present invention.

FIG. 3 is a block diagram illustrating different embodiments for determining a time measure in accordance with the present invention. In FIG. 3 a number of different measurement units is disclosed, but it should be understood that, in use, preferably, one or two units are used. Two units may be used if different measurement techniques are used to detect the start and the end of the time period.

In one embodiment an impedance measurement unit is used to determine the blood pressure reflection wave measure t by identifying specified parts of impedance waveforms obtained by the impedance measurement unit.

In the following some general aspects of pressure and impedance measurements are discussed which are applicable also when determining DDP and SAP.

Figure 9:
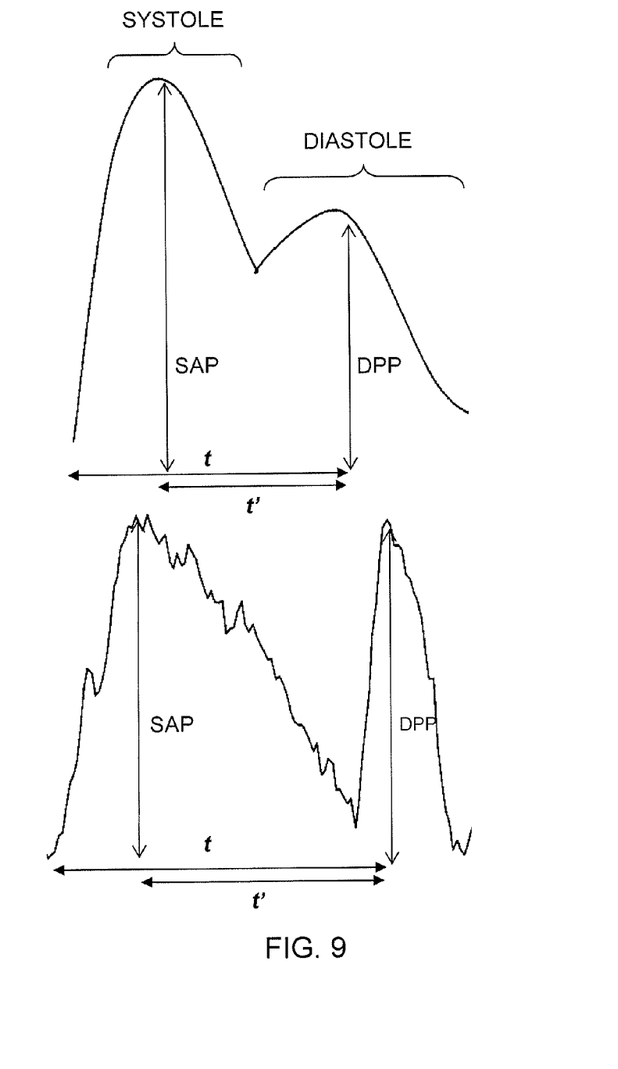
FIG. 9 shows a pressure waveform (upper curve) and an impedance waveform (lower curve) used to determine the parameters of the CPI equation.

The upper curve of FIG. 9 schematically illustrates the aortic blood pressure close to the aortic valve. The lower curve illustrates an impedance signal obtained by the set up illustrated in FIG. 11.

Figure 11:
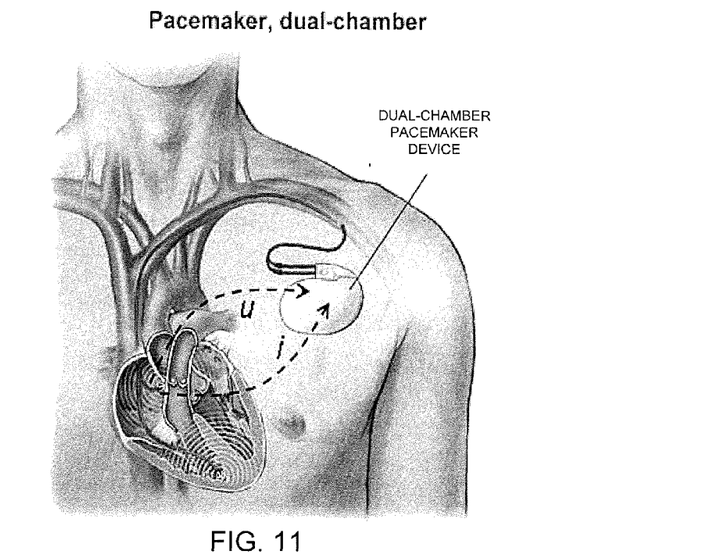
FIG. 11 shows a patient having an implanted heart stimulator used to obtain impedance signals.

In FIG. 11 is shown how the impedance is recorded between the electrodes in the right atrium and the pacemaker can in order to monitor the aortic valve closure, for instance tripolar impedance configuration using the RA-ring and RA-tip in connection with the device can (capsule or housing) as nodes for current injection and voltage sensing. This means that the resulting voltage which is measured during injection of the excitation current will be across the aorta and that the resulting impedance signal contains information pertaining to the aorta.

Figure 12:
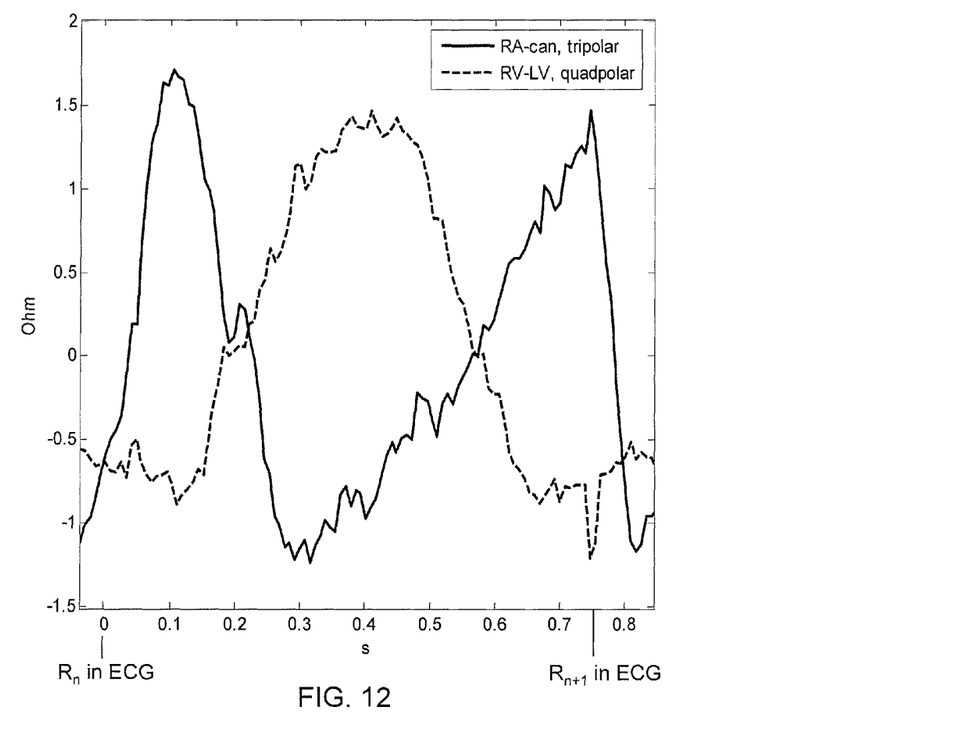
FIG. 12 shows two different impedance waveforms.

In FIG. 12, tripolar impedance measuring aortic properties is displayed together with impedance waveform using a right ventricle-left ventricle quadropolar configuration. This latter configuration is predominantly acquiring left ventricular properties. As can be expected, the tripolar impedance measuring aortic properties is in opposite phase when compared to an impedance measurement monitoring the left ventricle for instance.

The solid line represents the impedance discussed above, whereas the dashed impedance waveform represents a more "standard" intracardiac impedance, e.g. obtained between electrodes in right and left ventricles. The dashed waveform will increase during systole as blood is ejected from the heart and decrease as blood returns during diastole, due to the higher conductivity of blood than the surrounding tissue. In the case with the impedance discussed in relation to the present invention is the opposite. This would suggest that we measure an increased blood volume during systole. Thus, this observation in connection with the information from FIG. 11 is a strong indication that in fact the aorta is measured.

Certain characteristics in the aortic pressure waveform are of interest in connection with the present invention which will be described in the following.

In FIG. 9, in which the impedance waveform has been inverted, also a schematic aortic pressure waveform is shown. In addition to t also the other parameters of the CPI-equation are indicated in the Figure.

In the upper part of FIG. 9 the aortic pressure curve close to the aortic valve is shown. During systolic contraction of the left ventricle the aortic valve is open. During diastole the left ventricle relaxes and the valve is closed. The connections to the aorta of the two coronary arteries are situated in aorta close to the aortic valve. Flow in the coronary arteries supplying the left ventricle is close to zero during systole due to high wall tension and collapse of small intramyocardial blood vessels. The diastolic pressure is therefore of great importance for myocardial vascular supply.

According to an embodiment of the present invention the time period ends at the local maximum of blood pressure following aortic valve closure, which is determined from the inverted impedance curve form as the point of time of the second maximum of the inverted impedance waveform, which is illustrated in FIG. 9.

Figure 10A:
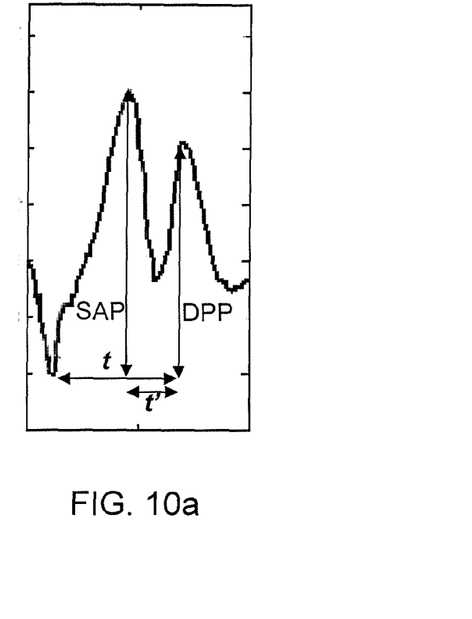
FIGS. 10a-10c show impedance waveforms illustrating the present invention.
Figure 10B:
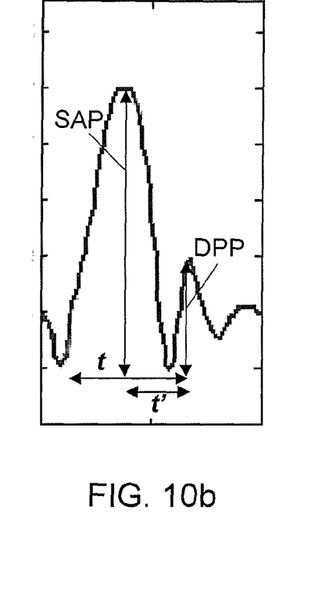
Figure 10C:
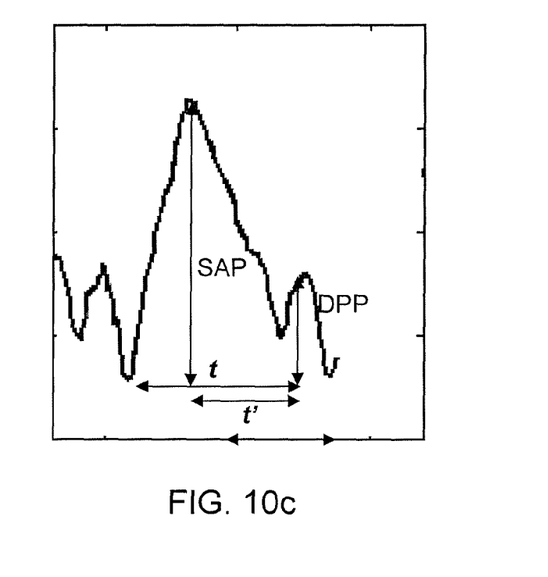

The preset point of time starting the time period is, according to one embodiment, the point in time where the first maximum of the inverted impedance waveform ($d(-Z)/dt$) occurs following the R-wave, where Z is the impedance measured by the impedance measurement unit. In FIG. 9 (lower curve) the time period length determined according to this embodiment is denoted t'. FIGS. 10a-10c show further examples of impedance curves were t, t', SAP and DDP are indicated. The impedance curve shown in FIG. 10c is obtained by applying the current between the ring electrode in the right atrium and the housing of the pacemaker (the case), and the voltage is sensed between the tip electrode in the right atrium and the case.

In another embodiment a blood pressure measurement unit is used to determine the blood pressure reflection wave measure t by identifying specified parts of pressure waveforms obtained by that unit.

According to one embodiment the time period ends at the point of time of the second arterial pressure maximum of the reflected wave following aorta valve closure.

The preset point of time starting the time period is the point of time where the maximum of $dLVP/dt$ occurs, where LVP is the blood pressure in the left ventricle measured by the blood pressure measurement unit.

This is illustrated by the upper curve of FIG. 9 and the time period is indicated by t'.

In another embodiment the preset point of time starting the time period is the time of opening of the aortic valve following an R-wave. In still another embodiment the closure of the AV-valves, i.e. the mitralis and/or tricuspidalis valves, may be used as starting points.

The point of time of opening and/or closing of the valves is in one embodiment determined by using a heart sound measurement unit. If measuring the closure of the AV-valves preferably the first heart tone (S1) is used.

In still another embodiment the point of time of opening of the aortic valve is determined by using a blood flow measurement unit adapted to measure the blood flow in the left ventricle or in the arterial system. The time period then ends at the point of time at which a second maximum is sensed going in the other direction compared to the direction of the primary pulse started by the mechanical systole.

The time of opening of the aortic valve following the R-wave may as an alternative be determined by using a pulse plethysmography (PPG) measurement unit adapted to measure the onset of blood flow following the onset of electrical systole, and that the time period ends at the point of time of a second maximum detectable in a PPG-signal detected by said PPG measurement unit.

In still another embodiment the preset point of time starting the time period is the point of time for the R-wave using an IEGM detecting unit. The time period in this case is indicated by t in the upper curve of FIG. 9.

A further alternative is to use as a starting point the point in time coinciding with the first pressure maximum, or inverted impedance maximum, following the R-wave. Herein the situation might occur that t becomes negative which may be the case of very quick reflecting pressure waves.

Furthermore, an indirect measure of t may also be obtained through an estimate of vessel elasticity. An increased elasticity in the arterial system of the patient will inevitably lead to a prolongation of t, whereas a decrease in elasticity will cause a faster return of the reflected pressure wave, causing a decrease in t.

Diastolic Peak Pressure—DPP

Figure 6:
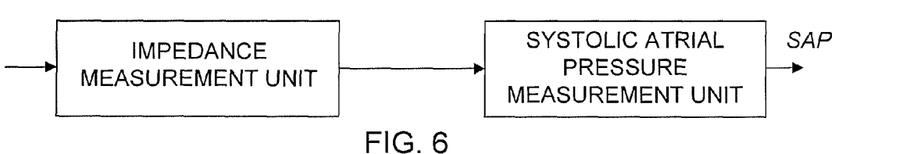
FIGS. 6 and 7 are block diagrams illustrating different embodiments of determining SAP according to the present invention.

In order to determine DPP a blood pressure measurement unit is arranged in accordance with one embodiment of the present invention. This is schematically illustrated in FIG. 6. The blood pressure measurement unit is adapted to measure the blood pressure in the arterial system close to the aortic valve, and by determining DPP as the peak-to-peak value for the second maximum in the heart cycle from obtained pressure signals which is shown in the upper curve of FIG. 9.

In an alternative embodiment the blood pressure measurement unit is adapted to measure the blood pressure in the arterial system close to the aortic valve, and to determine DPP by integration of the pressure signal waveform during diastole.

Figure 4:
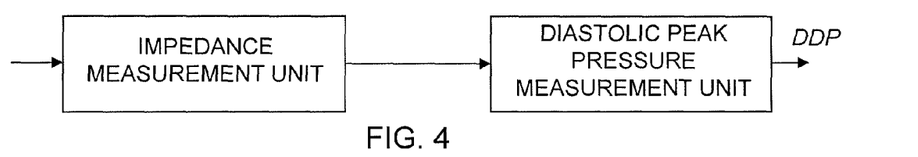
FIGS. 4 and 5 are block diagrams illustrating different embodiments of determining DDP according to the present invention.
Figure 5:
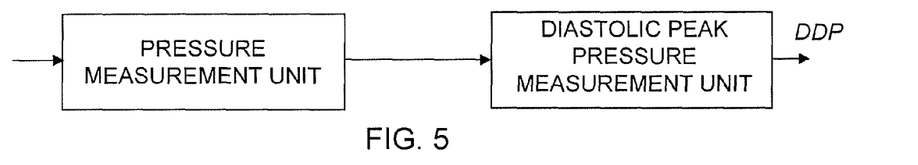

In another embodiment the device comprises an impedance measurement unit adapted to determine the DPP as the amplitude of the local maximum of the impedance during diastole. A block diagram of this embodiment is shown in FIG. 4, and in the lower curve of FIG. 9 is indicated how to identify DPP from the impedance curve.

Figure 13:
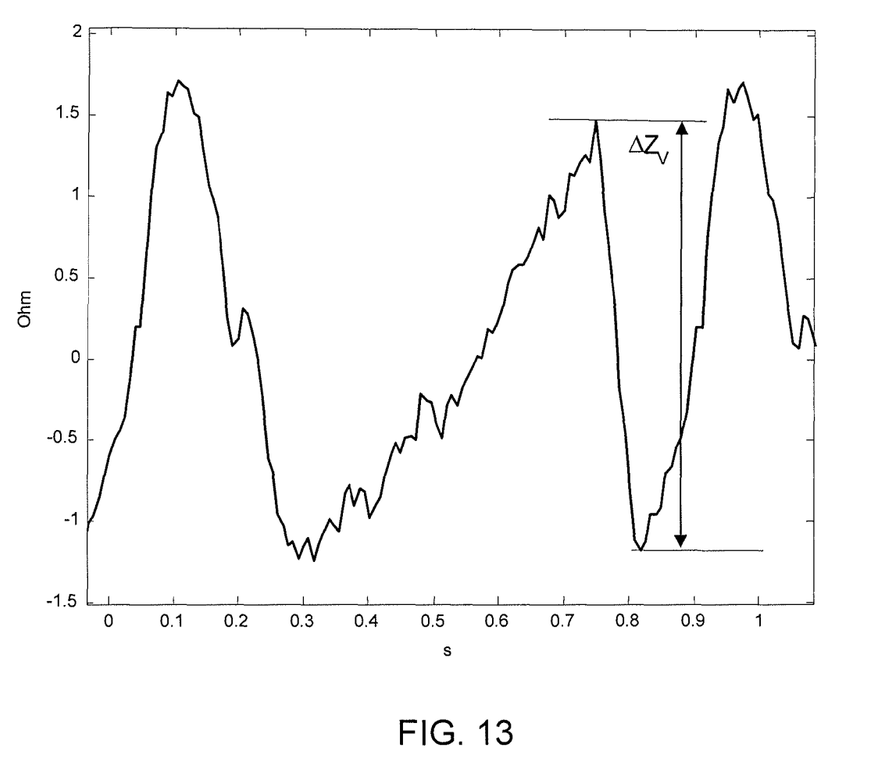
FIG. 13 shows an impedance waveform and how DPP may be obtained from that waveform.

Also FIG. 13 shows an impedance waveform where DPP is determined by identifying the peak to peak impedance value during diastole, indicated in FIG. 13 as $\Delta Z_v$. For example by performing a peak-to-peak calculation in a given window after a detected R-wave.

Still another possibility is to use photoplethysmography or impedance in direct connection to the main coronary arteries as approximation for DPP, considering that the DPP is supposed to be a measure of blood supply to the heart itself.

Another alternative is to use a flow sensor in connection to the main coronary artery and then detecting the peak value.

Systolic Arterial Pressure—SAP

Figure 7:
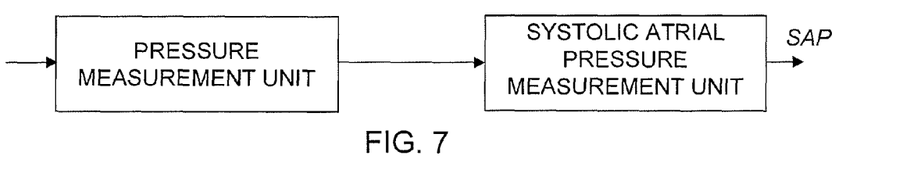
Figure 8:
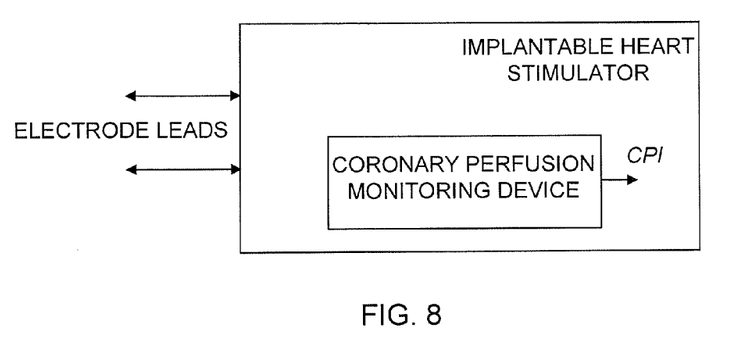
FIG. 8 is a block diagram illustrating the coronary perfusion monitoring device in connection with an implantable heart stimulator.

The systolic arterial pressure SAP is the absolute blood pressure above atmospheric pressure. SAP is determined most effectively by using a pressure sensor in the arterial system, preferably close to the aortic valve. Thus, in accordance with a preferred embodiment the implantable coronary perfusion monitoring device, according to the present invention, comprises a blood pressure measurement unit adapted to measure the blood pressure in the arterial system in the aorta or in the left ventricle, and that determines SAP as the first maximum pressure value following the onset of electrical systole. A block diagram illustrating this embodiment is shown in FIG. 7. The upper curve of FIG. 9 illustrates how SAP is determined from the pressure curve.

If a continuous pressure waveform is available SAP may be calculated by integrating the waveform during systole.

In another embodiment the device comprises an impedance measurement unit adapted to determine the SAP as the first maximum peak to peak value of the inverted impedance signal, occurring after onset of electrical systole. This embodiment is illustrated by the block diagram in FIG. 6 and indicated in the lower curve in FIG. 9.

As a further alternative a photoplethysmography sensor may be used, which has the benefit that it does not need to be arranged in the arterial system, but only adjacent to it. By using the pulsating blood flow SAP may be determined.

By using a flow sensor in the left ventricle or in the aorta, or adjacent to any of the main arteries, and using the peak value following the onset of electrical systole an estimate of SAP will be obtained.

The CPI values may be calculated at regular intervals, or upon request, and in that regard the device further comprises a CPI processing unit adapted to store calculated CPI values in order to e.g. identify long term trends of the CPI values. The CPI processing unit may e.g. be provided with one or many threshold values indicative of specific perfusion states. The CPI processing unit may then be adapted to generate CPI alert signals in dependence of the CPI values relation to the threshold or thresholds.

One preferred implementation of the implantable coronary perfusion monitoring device according to the present invention is to arrange the device in connection to an implantable heart stimulator provided with one or many electrode leads adapted to apply stimulation therapy to the heart.

If implemented in an implantable heart stimulator the CPI processing unit is adapted to detect variations of the CPI values as a result of variation of the stimulation therapy and then being able to optimize the stimulation therapy such that the CPI is as high as possible.

The implantable heart stimulator including the coronary perfusion monitoring device is naturally provided with all necessary means required to perform its intended stimulation therapy. Among those means may be mentioned telemetry means which enables bi-directional wireless communication between the stimulator and an external programming device. It is then possible, in addition to all other information sent to, and received from, the stimulator to also include CPI values and values related to CPI values.

Although modifications and changes may be suggested by those skilled in the art, it is the intention of the inventors to embody within the patent warranted heron all changes and modifications as reasonably and properly come within the scope of their contribution to the art.

We claim as our invention:

1. Implantable coronary perfusion monitoring device for in-vivo determination of a coronary perfusion index (CPI) indicative of the coronary perfusion of a heart, said device comprising:

a systolic arterial pressure measurement unit configured to determine a systolic arterial blood pressure measure SAP related to systolic arterial pressure;

a diastolic peak pressure measurement unit configured to determine a diastolic peak blood pressure measure DPP related to diastolic aortic peak pressure representing a reflected blood pressure wave;

a time measurement unit configured to determine a blood pressure reflection wave measure t indicating a timely position in the heart cycle of the maximum of a reflected blood pressure wave in a time period starting at a preset point of time in systole and ending at a local maximum of blood pressure following aortic valve closure, and a coronary perfusion index calculating unit configured to determine said coronary perfusion index CPI as (t·DPP)/SAP.

2. Implantable coronary perfusion monitoring device according to claim 1 comprising an impedance measurement unit that detects waveforms, and wherein said time measurement unit is configured to determine said blood pressure reflection wave measure t by identifying specified parts of said impedance waveforms.

3. Implantable coronary perfusion monitoring device according to claim 2, wherein said time measurement is configured to use, as said preset point of time starting the time period a point in time where a first max d(−Z)/dt occurs following an R-wave of the heart, where Z is an impedance measured by the impedance measurement unit.

4. Implantable coronary perfusion monitoring device according to claim 2, wherein said time measurement is configured to end said time period at a point of time of the second maximum of the inverted impedance waveform.

5. Implantable coronary perfusion monitoring device according to claim 2, comprising a pulse plethysmography (PPG) unit and wherein the time measurement unit is configured to determine the time of opening of the aortic valve following the R-wave using an onset of blood flow following the onset of electrical systole measured by said PPG unit.

6. Implantable coronary perfusion monitoring device according to claim 5, wherein said time measurement is configured to end said time period at the point of time of a second maximum detectable in a PPG-signal detected by said PPG measurement unit.

7. Implantable coronary perfusion monitoring device according to claim 1 comprising a blood pressure measurement unit that detects pressure waveforms, and wherein said time measurement unit is configured to determine said blood pressure reflection wave measure t by identifying specified parts, representing start and end parts of the time period, of said pressure waveforms.

8. Implantable coronary perfusion monitoring device according to claim 7, wherein said time measurement is configured to use, as said preset point of time starting the time period, a point of time where the maximum of dLVP/dt occurs, where LVP is the blood pressure in the left ventricle measured by said blood pressure measurement unit.

9. Implantable coronary perfusion monitoring device according to claim 7, wherein said time measurement is configured to end said time period at a point of time of the second arterial pressure maximum of the reflected wave following aorta valve closure.

10. Implantable coronary perfusion monitoring device according to claim 1, wherein said time measurement is configured to use, as said preset point of time starting the time period, a time of opening of the aortic valve following an R-wave.

11. Implantable coronary perfusion monitoring device according to claim 10, comprising a heart sound measurement unit that determines the point of time of opening of the aortic valve.

12. Implantable coronary perfusion monitoring device according to claim 10, comprising a blood flow measurement unit adapted to measure the blood flow in the left ventricle or in the arterial system that determines the point in time of opening of the aortic valve.

13. Implantable coronary perfusion monitoring device according to claim 12, wherein said time measurement is configured to end said time period at the point of time at which a second maximum is sensed going in an opposite direction compared to a direction of the primary pulse started by the mechanical systole.

14. Implantable coronary perfusion monitoring device according to claim 1, comprising an intracardiac electrogram (IEGM) detecting unit and wherein said time measurement is configured to use, as said preset point of time starting the time period, a point of time for an R-wave identified in an IEGM detected by said IEGM detecting unit.

15. Implantable coronary perfusion monitoring device according to claim 1 comprising a blood pressure measurement unit that measures blood pressure in the arterial system close to the aortic valve, and wherein DPP is determined as the peak-to-peak value for the second maximum in the heart cycle from obtained pressure signals.

16. Implantable coronary perfusion monitoring device according to claim 1 comprising a blood pressure measurement unit that measures blood pressure in the arterial system close to the aortic valve, and wherein DPP is determined by integration of the pressure signal during diastole.

17. Implantable coronary perfusion monitoring device according to claim 1 comprising an impedance measurement unit that determines DPP as an amplitude of a local maximum of impedance during diastole.

18. Implantable coronary perfusion monitoring device according to claim 1 comprising a blood pressure measurement unit that measures blood pressure in the arterial system in the aorta or in the left ventricle, and wherein SAP is determined as a first maximum pressure value following onset of electrical systole.

19. Implantable coronary perfusion monitoring device according to claim 1 comprising an impedance measurement unit that determines SAP as a first maximum peak to peak value of an inverted impedance signal, occurring after onset of electrical systole.

20. Implantable coronary perfusion monitoring device according to claim 1, comprising a CPI processing unit that stores calculated CPI values and identifies long term trends of the CPI values.

21. Implantable coronary perfusion monitoring device according to claim 20, wherein said CPI processing unit is provided with one or more threshold values indicative of specific perfusion states, and the CPI processing unit generates CPI alert signals in dependence of the CPI values relation to said threshold or thresholds.

22. Implantable coronary perfusion monitoring device according to claim 1, comprising a heart stimulator provided with at least one electrode lead configured to apply stimulation therapy to the heart dependent on said coronary perfusion index.

23. Implantable coronary perfusion monitoring device according to claim 22, wherein said CPI processing unit is configured to detect variations of the CPI values as a result of variation of the stimulation therapy.

24. Implantable coronary perfusion monitoring device according to claim 23, wherein said heart stimulator is configured to optimize said stimulation therapy to make the CPI as high as possible.

* * * * *